United States Patent
Chudzik et al.

(10) Patent No.: US 6,410,044 B1
(45) Date of Patent: Jun. 25, 2002

(54) CROSSLINKABLE MACROMERS

(75) Inventors: Stephen J. Chudzik, St. Paul; David L. Clapper, Shorewood, both of MN (US)

(73) Assignee: Surmodics, Inc., Eden Prairie, MN (US)

( * ) Notice: Subject to any disclaimer, the term of this patent is extended or adjusted under 35 U.S.C. 154(b) by 0 days.

(21) Appl. No.: 09/571,525

(22) Filed: May 16, 2000

Related U.S. Application Data

(60) Continuation-in-part of application No. 09/469,976, filed on Dec. 21, 1999, now Pat. No. 6,156,345, which is a division of application No. 09/121,248, filed on Jul. 23, 1998, now Pat. No. 6,007,833.
(60) Provisional application No. 60/078,607, filed on Mar. 19, 1998.

(51) Int. Cl.⁷ ............................. A61F 2/06; A61F 2/28; A61F 13/00; A61F 47/30
(52) U.S. Cl. ..................... 424/423; 424/445; 424/486; 424/488; 602/48; 602/49; 602/50; 602/54; 623/1.36; 623/1.46; 623/1.47; 623/1.48; 623/23.59; 623/23.6; 623/920; 623/921; 623/923; 623/926
(58) Field of Search ............................. 602/48, 49, 50, 602/51, 52, 54, 55, 56, 57; 623/1.36, 1.46, 1.47, 1.48, 5.16, 6.61, 6.62, 11, 15, 16, 23.59, 23.6, 920, 921, 923, 926; 530/354, 355, 356, 362, 363, 364, 409, 410; 536/1.11, 21, 102, 106, 112, 123.1, 124; 424/423, 424, 425, 443, 444, 445, 447, 448, 484, 485, 486, 487, 488; 435/177, 178, 179, 180, 181, 182; 156/275.5, 326, 327, 328, 329, 330, 331.1, 331.2, 331.3, 331.4, 331.5, 331.6, 331.7, 331.8, 331.9, 332, 333, 334, 335, 336, 337, 338; 525/50, 54.1, 54.3, 54.31; 522/34, 35, 87, 88, 109, 110, 111, 112, 904, 905

(56) References Cited

U.S. PATENT DOCUMENTS

| | | | |
|---|---|---|---|
| 3,879,353 A | 4/1975 | Crawford | 522/60 |
| 4,315,998 A | 2/1982 | Neckers et al. | 525/332 |
| 4,477,326 A | 10/1984 | Lin | 528/15 |
| 4,594,400 A | 6/1986 | Kvita et al. | 526/256 |
| 4,758,611 A | 7/1988 | Beers | 523/212 |
| 5,118,779 A | 6/1992 | Szycher | 528/75 |
| 5,213,580 A | 5/1993 | Slepian et al. | 623/1 |
| 5,232,984 A | 8/1993 | Hubbell et al. | 525/54 |
| 5,334,640 A | 8/1994 | Desai et al. | 524/56 |
| 5,380,536 A | 1/1995 | Hubbell et al. | 424/497 |
| 5,391,406 A | 2/1995 | Ramharack et al. | 427/516 |
| 5,410,016 A | 4/1995 | Hubbell et al. | 528/354 |
| 5,527,925 A | 6/1996 | Chabrecek | 549/430 |
| 5,529,914 A | 6/1996 | Hubbell et al. | 435/182 |
| 5,552,452 A | 9/1996 | Khadem et al. | 522/63 |
| 5,573,934 A | 11/1996 | Hubbell et al. | 435/177 |
| 5,575,815 A | 11/1996 | Slepian et al. | 623/1 |
| 5,612,050 A | 3/1997 | Rowe et al. | 424/423 |
| 5,723,513 A | 3/1998 | Bonham et al. | 522/63 |
| 5,846,530 A | 12/1998 | Soon-Shiong et al. | 424/93.7 |
| 5,858,746 A | 1/1999 | Hubbell et al. | 435/177 |
| 6,007,833 A | * 12/1999 | Chudzik et al. | 424/425 |
| 6,156,345 A | * 12/2000 | Chudzik et al. | 424/484 |

FOREIGN PATENT DOCUMENTS

| | | | |
|---|---|---|---|
| WO | 96/40829 | * 12/1996 | |
| WO | WO 97/24376 | 7/1997 | |

OTHER PUBLICATIONS

"Radical Polymerization", C.H. Bamford, pp. 940–957 in Kroschwitz, ed., Concise Encyclopedia of Polymer Science and Engineering, 1990.

* cited by examiner

*Primary Examiner*—Jeffrey E. Russel
(74) *Attorney, Agent, or Firm*—Frederickson & Byron, P.A.

(57) ABSTRACT

A crosslinkable macromer system and related methods of preparing the system and using the system in the form of a crosslinked matrix between a tissue site and an implant article such as a tissue implant or on the porous surface of a prosthetic device. The macromer system includes two or more polymer-pendent polymerizable groups and one or more initiator groups (e.g., polymer-pendent initiator groups). The polymerizable groups and the initiator group (s), when polymer-pendent, can be pendent on the same or different polymeric backbones. The macromer system provides advantages over the use of polymerizable macromers and separate, low molecular weight initiators, including advantages with respect to such properties as nontoxicity, efficiency, and solubility. A macromer system of the invention can be used as an interface between the tissue site and implant article in a manner sufficient to permit tissue growth through the crosslinked matrix and between the tissue site and implant. In a preferred embodiment, polymers with pendent polymerizable groups, for use in the macromer system, are prepared by reacting a polysaccharide polymer with a reactive moiety in an organic, polar solvent such as formamide.

20 Claims, No Drawings

CROSSLINKABLE MACROMERS

CROSS REFERENCE TO RELATED APPLICATIONS

The present application is a continuation-in-part of U.S. Ser. No. 09/469,976 (now U.S. Pat. No. 6,156,345), filed Dec. 21, 1999, which is a divisional of U.S. patent application filed Jul. 23, 1998 and assigned Ser. No. 09/121,248 (now U.S. Pat. No. 6,007,833), which claims the benefit of provisional U.S. patent application filed Mar. 19, 1998 and assigned Ser. No. 60/078,607, the entire disclosures of which are incorporated herein by reference.

TECHNICAL FIELD

The present invention relates to the preparation of matrices by the polymerization of macromers. In another aspect, the invention relates to the use of such matrices for such purposes as cell immobilization, tissue adherence, and controlled drug delivery.

BACKGROUND OF THE INVENTION

Matrices are polymeric networks characterized by insolubility in water. One type of polymeric matrix is a hydrogel, which can be defined as a water-containing polymeric network. The polymers used to prepare hydrogels can be based on a variety of monomer types, such as those based on methacrylic and acrylic ester monomers, acrylamide (methacrylamide) monomers, and N-vinyl-2-pyrrolidone. To form the gel, these monomer classes are typically crosslinked with such crosslinking agents as ethylene dimethacrylate, N,N'-methylenebisacrylamide, methylenebis(4-phenyl isocyanate), ethylene dimethacrylate, divinylbenzene, and allyl methacrylate.

Another type of polymeric network can be formed from more hydrophobic monomers and/or macromers. Matrices formed from these materials generally exclude water. Polymers used to prepare hydrophobic matrices can be based on a variety of monomer types such as alkyl acrylates and methacrylates, and polyester-forming monomers such as ε-caprolactone and lactide. When formulated for use in an aqueous environment, these materials do not need to be crosslinked, but they can be crosslinked with standard agents such as divinyl benzene. Hydrophobic matrices can also be formed from reactions of macromers bearing the appropriate reactive groups such as the reaction of diisocyanate macromers with dihydroxy macromers, and the reaction of diepoxy-containing macromers with dianhydride or diamine-containing macromers.

Although there exist a variety of methods for producing polymeric networks, when these networks are intended to be created in the presence of viable tissue, and/or to contain a bioactive compound, the number of acceptable methods of producing polymeric networks is extremely limited.

It is nevertheless desirable to form both hydrogel and non-hydrogel polymeric matrices in the presence of viable tissue or bioactive agents for the purposes of drug delivery, cellular immune isolation, prevention of post-surgical adhesions, tissue repair, and the like. These polymeric matrices can be divided into two categories: biodegradable or bioresorbable polymer networks and biostable polymer networks.

Biodegradable polymeric matrices have been previously suggested for a variety of purposes, including controlled release carriers, adhesives and sealers. When used as controlled release carriers, for instance, polymeric matrices can contain and release drugs or other therapeutic agents over time. Such matrices can be formed, for instance, by a number of different processes, including solvent casting hydrophobic polymers. Solvent casting, however, typically involves the use of organic solvents and/or high temperatures which can be detrimental to the activity of biological materials and can complicate production methods. Solvent casting of polymers out of solution also results in the formation of uncrosslinked matrices. Such matrices have less structure than crosslinked matrices and it is more difficult to control the release of bioactive agents from such matrices. Yet another process, which involves the polymerization of monomers in or around the desired materials, suffers from cytotoxicity of monomers, oxygen inhibition and heat of polymerization complications.

Another process used in the past to prepare biodegradable and biostable hydrogels involves the polymerization of preformed macromers using low molecular weight initiators. This process involves a number of drawbacks as well, however, including toxicity, efficacy, and solubility considerations. For instance, when using a macromer solution containing a low molecular weight soluble initiator to encapsulate viable cellular material, the initiator can penetrate the cellular membrane and diffuse into the cells. The presence of the initiator may involve some toxic consequence to the cells. When activated, however, these initiators produce free radicals having distinct cytotoxic potential. Other drawbacks arise if the initiator is able to diffuse out of the formed matrix, thereby producing toxicity and other issues. Such initiators also tend to aggregate in aqueous solution, causing efficiency and reproducibility problems. Finally, in view of the limited efficiency of many initiators for initiating the necessary radical chain polymerization, it is often necessary to add one or more monomeric polymerization "accelerators" to the polymerization mixture. Such accelerators tend to be small molecules capable of penetrating the cellular membrane, and often raise cytotoxic or carcinogenic concerns.

U.S. Pat. Nos. 5,410,016 (Hubbell, et al.) and 5,529,914 (Hubbell, et.al.) for instance, relate to hydrogels prepared from biodegradable and biostable polymerizable macromers. The hydrogels are prepared from these polymerizable macromers by the use of soluble, low molecular weight initiators. Such initiators can be combined with the macromers, and irradiated in the presence of cells, in order to form a gel that encapsulates the cells. A considerable number of similar and related patents have arisen over recent years. See, for instance, U.S. Pat. Nos. 5,232,984; 5,380,536; 5,573,934; 5,612,050; 5,837,747; 5,846,530; and 5,858,746.

Hydrogels often suffer from similar or other drawbacks in use as biological adhesives or sealants, e.g., for use as tissue adhesives, endovascular paving, prevention of post-surgical adhesions, etc. In each of the applications, the hydrogel matrix must generally "adhere" to one or more tissue surfaces. Current methods rely upon physical "adhesion" or the tendency of hydrogels to "stick" to a surface. A superior adhesive would provide both physical and chemical adhesion to surfaces utilizing the same physical characteristics as current hydrogel adhesives, but also providing chemical, covalent coupling of the matrix material to the tissue surface. Covalent bonds are generally much stronger than physical adhesive forces, such as hydrogen bonding and van der Waals forces.

As described above, when various techniques are used to form polymeric matrices via photoinitiation of macromers, the photoinitiators utilized tend to be low molecular weight.

Polymeric photoinitiators have been described as well, although for applications and systems quite distinct from those described above. See, for instance, "Radical Polymerization", C. H. Bamford, pp. 940–957 in Kroschwitz, ed., Concise Encyclopedia of Polymer Science and Engineering, 1990. In the subsection entitled "Photosensitized Initiation: Polymeric Photosensitizers and Photoinitiators", the author states that "[p]olymeric photosensitizers and photoinitiators have been described. Many of these are polymers based on benzophenone, e.g., poly(p-divinylbenzophenone) (DVBP). Such rigid polymers are reported to be effective sensitizers since hydrogen abstraction from the backbone by excited benzophenone is less likely."

U.S. Pat. No. 4,315,998 (Neckers) describes polymer-bound photosensitizing catalysts for use in the heterogeneous catalysis of photosensitized chemical reactions such as photo-oxidation, photodimerization, and photocyclo addition reactions. The polymer-bound photosensitizing catalysts are insoluble in water and common organic solvents, and therefore can be readily separated from the reaction medium and reaction products by simple filtration.

What is clearly needed are macromers and macromer systems that avoid the problems associated with conventional polymeric matrices, and in particular, those drawbacks that arise when polymeric matrices are formed in the presence of viable tissue or bioactive agents.

SUMMARY OF THE INVENTION

The present invention provides a method of improving the performance, within a host tissue site, of an implanted article (e.g., implanted tissue or implanted prosthetic device providing a porous surface), by promoting the growth of continuous tissue between host tissue and the implant. An implanted article of this invention can be provided, for instance, in the form of cultured tissue and/or native tissue (e.g., transplanted tissue), or can be fabricated from polymeric and/or metallic materials. The method employs a crosslinkable macromer system adapted to form an interface between the article and the host tissue, in order to facilitate (e.g., promote and/or permit) tissue integration by the body between the implant and the tissue site, e.g., into and through the crosslinked macromer and into the porosity of a porous device surface.

Applicant's parent application Ser. No. 09/121,248 (now U.S. Pat. No. 6,007,833) provides examples of preferred macromer systems useful in the method of the present invention. The parent application teaches the use of such systems for various applications, including cellular encapsulation, adhesives and sealants, barriers, controlled release carriers, tissue replacement/scaffolding, wound dressings, and in situ device formation. For use in tissue replacement, for instance, the parent application teaches the placement of a macromer system in a mold or cavities in a device.

Polymeric matrices of this invention (as formed by crosslinking the macromer system) can be used, for instance, to improve the tissue response to implanted medical devices. Examples of improved tissue response include: 1) increased tissue ingrowth (e.g., into the pores of cementless hip implants), and, 2) decreased fibrosis (e.g., around breast implants and hernia repair meshes). In addition to tissue integration, the macromer system can provide a variety of advantages, including a reduction in both immediate and chronic adverse reactions to the device (e.g., thereby preventing the accumulation of fluid and/or undesirable cells) by virtue of the immediate and desirable space filling characteristics.

A macromer system of this invention can be provided between the implant and tissue site in any suitable manner, e.g., the system can be provided upon the surface of the implant before, during and/or after placement of the implant in the tissue site. Similarly, the macromer system(s) can be polymerized to form a matrix at any suitable point, e.g., a system can be coated on an implant, and/or delivered to the tissue site, and crosslinked either before, during and/or after positioning the implant in or upon the tissue site. For example, a system can be provided and crosslinked on the surface of a prosthetic device, e.g., by either the manufacturer or surgeon, and implanted into the tissue site. As another example, a macromer system can be applied to the tissue site itself, polymerized in situ (e.g., by the application of illumination either directly to the system or through translucent tissue), and an implant article (with or without a macromer system or matrix on its surface) positioned on or in the site.

The resulting combination of implant and matrix within the tissue site, permits the formation of continuous tissue growth, over time, through the matrix and between the implant and tissue site. Such growth can be unidirectional (e.g., originating from the tissue site toward the implant) and/or bidirectional (e.g., originating from both the tissue site and from an implanted tissue).

A system, or resultant matrix, can be applied with or without additional components, such as growth factors, morphogenic factors, or DNA. Both degradable and non-degradable macromer systems are useful, but matrices adapted to degrade with desired kinetics, are preferred.

In another aspect, the present invention provides a combination comprising an implant article, such as a tissue implant or prosthetic device having one or more porous surfaces, and a matrix formed of a crosslinked macromer system as described herein. In one embodiment, the article and uncrosslinked macromer system are initially combined (e.g., the system coated on the article) outside the body, thereby permitting the system to be crosslinked prior to, during and/or following placement of the implant within the body site. In an alternative embodiment, the combination is provided by positioning an article within and/or in apposition to the body site, and delivering the macromer system to the body site (before, during and/or after placement of the article itself), where it is crosslinked as a sufficiently stable coating or other suitable interface in its position between the article and the tissue site.

For instance, a macromer system in liquid (e.g., substantially flowable) form can be applied to a tissue defect, before, during or after which a tissue implant or preformed device is pressed into the defect. The system can be provided, for instance, to occupy a space of between about 0.1 mm to about 10 mm between the implant and the tissue site. The system is illuminated in order to activate the initiator groups and thus polymerize the macromer system into a solid matrix. The resultant combination of tissue implant or preformed device, together with crosslinked macromer system, completely and conformally fills the defect such that no gaps remain for the accumulation of undesirable fluids or cells.

As described herein, the macromer system can thus be used in the manner of a "grout", for instance, to fill the spaces between a tissue implant or preformed device (itself either tissue-based or non-tissue based) and adjacent tissue. Current tissue implants include, for instance, both those obtained as transplants (e.g., autografts, allografts or xenografts) and those provided by tissue engineering. Current tissue engineering products often consist of cultured tissues that are implanted into tissue defects. Such products do not typically conform well to adjacent native tissue, however, thus leaving spaces into which undesirable fluids and cells can accumulate and produce adverse tissue responses. For example, when cultured cartilage is implanted into cartilage defects, synovial fluid and macrophages can enter the unfilled space and lead to fibrous tissue formation, which prevents integration of the implanted cartilage with the native cartilage. Other cultured tissues that are implanted into tissue defects, and that would benefit from the present macromer system applied as a grout include, but are not limited to, skin, bone, ligaments, blood vessels, and heart valves.

Implants, e.g., prosthetic devices, useful in a combination or method of this invention include those in which tissue integration is desired, and that themselves provide (or can be provided with) a sufficiently porous surface that permits or facilitates tissue integration once positioned in vivo. Examples of suitable porous prosthetic devices include, but are not limited to; joint implants (e.g., for hip or knee reconstruction), dental implants, soft tissue cosmetic prostheses (e.g., breast implants), wound dressings, vascular prostheses (e.g., vascular grafts and stents), and ophthalmic prostheses (e.g., intracorneal lenses). The macromer system of this invention, in turn, can be used in any suitable manner, e.g., to coat and/or fill voids within or upon the surface of the prosthetic device.

Such devices preferably are themselves formed of or otherwise provide (or can be provided with) a surface having sufficient porosity to permit tissue ingrowth in vivo. As used herein, the word "porous", and inflections thereof, will refer to one or more portions of the device surface that are designed for direct or indirect contact with the surrounding natural tissue, sufficient to permit tissue integration into the porosity thereof. Porous surfaces can be provided in a variety of ways, e.g., as sintered particles on a surface, such as titanium particles on the surface of cementless hip implants, as are available from a variety of orthopedic companies. Porous surfaces can also be provided in the form of cavities that remain from mixing salt crystals with silicone rubber oligomers, then solidifying (vulcanizing) the silicone rubber, and finally dissolving the salt crystals (as currently done for a variety of breast implants). Yet other porous surfaces can be fabricated from fibrous materials or produced as porous sponges via solvent casting and particulate leaching, phase separation, or gas foaming (see, e.g., B. S. Kim and D. J. Mooney, Development of Biocompatible Synthetic Extracellular Matricies for Tissue Engineering TIBTECH 16:224–230 (1998)).

Such porous surfaces typically provide a three-dimensional structure of spaces into which tissue can grow and mature. Porous regions of an implantable device preferably have a high pore density, in that the pores themselves occupy a greater relative volume than the material forming and separating those pores. Desirably, the pores have interconnected passages that allow direct contact between the tissue growing in adjacent pores. The minimum average pore size is preferably sufficient to accommodate capillaries (e.g., of about 5 micron diameter) and the maximum average pore size is about 1 mm. Preferable pore sizes will vary from tissue to tissue and typically range from about 20 microns to about 600 microns, and more preferably from about 50 microns to about 400 microns.

A crosslinkable macromer system useful in the present invention comprises two or more polymer-pendent polymerizable groups and one or more initiators, preferably in the form of polymer-pendent initiator groups. In a preferred embodiment, the polymerizable groups and the initiator group(s) are pendent on the same polymeric backbone. In an alternative preferred embodiment, the polymerizable groups and initiator group(s) are pendent on different polymeric backbones.

In the first embodiment, the macromer system comprises a polymeric backbone to which are covalently bonded both the polymerizable groups and initiator group(s). Pendent initiator groups can be provided by bonding the groups to the backbone at any suitable time, e.g., either prior to the formation of the macromer (for instance, to monomers used to prepare the macromer), or to the fully formed macromer itself. The macromer system itself will typically comprise but a small percentage of macromers bearing both initiator groups and polymerizable groups. The majority of macromers will provide only pendent polymerizable groups, since the initiator groups are typically sufficient if present at far less than 1:1 stoichiometric ratio with macromer molecules.

In an alternative preferred embodiment, the macromer system comprises both polymerizable macromers, generally without pendent initiator groups, in combination with a polymeric initiator. In either embodiment, the initiator will be referred to herein as a "polymeric initiator", by virtue of the attachment of such initiator groups to a polymeric backbone. Yet another embodiment of this invention includes the macromer system having free (non-polymer bound) initiator molecules.

Macromer systems of the present invention, employing polymeric initiators, provide a number of unexpected advantages over the use of polymerizable macromers and separate, low molecular weight initiators. Such systems, for instance, provide an optimal combination of such properties as nontoxicity, efficiency, and solubility. Solubility, for instance, can be improved by virtue of the ability to control the aqueous or organic solubility of the polymerizable macromer by controlling the backbone. Toxicity can also be improved, since the polymeric initiators of this invention typically cannot diffuse into cells in the course of immobilization.

In a preferred embodiment, the pendent initiator groups are selected from the group consisting of long-wave ultra violet (LWUV) light-activatable molecules such as; 4-benzoylbenzoic acid, [(9-oxo-2-thioxanthanyl)-oxy]acetic acid, 2-hydroxy thioxanthone, and vinyloxymethylbenzoin methyl ether; visible light activatable molecules; eosin Y, rose bengal, camphorquinone and erythrosin, and thermally activatable molecules; 4,4' azobis(4-cyanopentanoic) acid and 2,2-azobis[2-(2-imidazolin-2-yl) propane] dihydrochloride. An important characteristic of the initiator group being the ability to be coupled to a preformed macromer containing polymerizable groups, or to be modified to form a monomer which can take part in the macromer synthesis, which is subsequently followed by the addition of polymerizable groups.

In such an embodiment, the pendent polymerizable groups are preferably selected from the group consisting of pendent vinyl groups, acrylate groups, methacrylate groups, ethacrylate groups, 2-phenyl acrylate groups, acrylamide groups, methacrylamide groups, itaconate groups, and styrene groups.

In a further preferred embodiment, the polymeric backbone is selected from the group consisting of synthetic macromers, such as polyvinylpyrrolidone (PVP), polyethylene oxide (PEO), and polyethylene glycol (PEG); derivatizable naturally occurring polymers such as cellulose; polysaccharides, such as hyaluronic acid, dextran, and heparin; and proteins, such as collagen, gelatin, and albumin.

The macromers of the present invention can be used in a variety of applications, including controlled drug release, the preparation of tissue adhesives and sealants, the immobilization of cells, and the preparation of three-dimensional bodies for implants. In one aspect, for instance, the invention provides a method for immobilizing cells, the method comprising the steps of combining a polymeric initiator of the present invention with one or more polymerizable macromers and in the presence of cells, under conditions suitable to polymerize the macromer in a manner that immobilizes the cells.

DETAILED DESCRIPTION

As used herein the following words and terms shall have the meaning ascribed below:

"macromer system" shall refer to a polymerizable polymer system comprising one or more polymers providing pendent polymerizable and initiator groups. Groups can be present either on the same or different polymeric backbones, e.g., on either a polymerizable macromer or a non-polymerizable polymeric backbone;

"polymerizable macromer" shall refer to a polymeric backbone bearing two or more polymerizable (e.g., vinyl) groups;

"initiator group" shall refer to a chemical group capable of initiating a free radical reaction, present as either a pendent group on a polymerizable macromer or pendent on a separate, non-polymerizable polymer backbone; and "polymeric initiator" shall refer to a polymeric backbone (polymerizable or non-polymerizable) comprising one or more initiator groups and optionally containing one or more other thermochemically reactive groups or affinity groups.

The polymeric backbone of this invention can be either synthetic or naturally-occurring, and includes a number of macromers previously described as useful for the preparation of polymeric matrices. Generally, the backbone is one that is soluble, or nearly soluble, in aqueous solutions such as water, or water with added organic solvent (e.g., dimethylsulfoxide) or can be rendered soluble using an appropriate solvent or combination of solvents. Alternatively, the polymeric backbone can be a material which is a liquid under ambient physiological conditions. Backbones for use in preparing biodegradable gels are preferably hydrolyzable under in vivo conditions.

In general, the polymeric backbones of this invention can be divided into two categories: biodegradable or bioresorbable, and biostable reagents. These can be further divided into reagents which form hydrophilic, hydrogel matrices and reagents which form non-hydrogel matrices.

Bioresorbable hydrogel-forming backbones are generally naturally occurring polymers such as polysaccharides, examples of which include, but are not limited to, hyaluronic acid (HA), starch, dextran, heparin, chondroitin sulfate, dermatan sulfate, heparan sulfate, keratan sulfate, dextran sulfate, pentosan polysulfate, and chitosan; and proteins (and other polyamino acids), examples of which include but are not limited to gelatin, collagen, fibronectin, laminin, albumin, elastin, and active peptide domains thereof. Matrices formed from these materials degrade under physiological conditions, generally via enzyme-mediated hydrolysis.

Hyaluronic acid, when derivatized with polymerizable groups in the manner described herein, provides a variety of advantages and benefits not heretofore known or achievable. Hyaluronic acid has conventionally been derivatized in aqueous conditions (see, e.g., Soon-Shiong (U.S. Pat. No. 5,837,747), Sakurai (U.S. Pat. No. 4,716,224), and Matsuda (U.S. Pat. No. 5,763,504). Occasional references have described the ability to derivatize hyaluronic acid under organic conditions (see, e.g., Della Valle, U.S. Pat. No. 5,676,964). In most, if not all, such approaches, however, the reaction mixtures are either suspensions, as opposed to true solutions, or the hyaluronic acid is itself pre-reacted (typically in a predominantly aqueous mixture) to enhance its solubility in organic solvents.

Applicants have discovered the manner in which hyaluronic acid, as well as other polysaccharides and polyamino acids (such as collagen) can be effectively derivatized in organic, polar, anhydrous solvents and solvent combinations. A particularly preferred solvent is formamide, and combinations of other solvents therewith. Functionally, the solvent or solvent system is one in which the polymer is sufficiently soluble and that permits its derivatization to the desired extent. The ability to derivatize such polymers in the manner of this invention provides a variety of unexpected benefits, and an optimal combination of such properties as preparation cost, controllability, and yield.

As exemplifed below, for instance, hyaluronic acid is reacted in formamide (and TEA, for pH control) with a reactive moiety in the form of glycidyl acrylate in order to derivatize the hyaluronic acid molecules with acrylate groups. The number and/or density of acrylate groups can be controlled using the present method, e.g., by controlling the relative concentration of reactive moiety to saccharide group content.

Bioresorbable matrix-forming backbones are generally synthetic polymers prepared via condensation polymerization of one or more monomers. Matrix-forming polymers of this type include polylactide (PLA), polyglycolide (PGA), polycaprolactone (PCL), as well as copolymers of these materials, polyanhydrides, and polyortho esters.

Biostable hydrogel matrix-forming backbones are generally synthetic or naturally occurring polymers which are soluble in water, matrices of which are hydrogels or water-containing gels. Examples of this type of backbone include polyvinylpyrrolidone (PVP), polyethylene glycol (PEG), polyacrylamide (PAA), polyvinyl alcohol (PVA), and the like.

Biostable matrix-forming backbones are generally synthetic polymers formed from hydrophobic monomers such as methyl methacrylate, butyl methacrylate, dimethyl siloxanes, and the like. These backbone materials generally do not possess significant water solubility but can be formulated as neat liquids which form strong matrices upon activation. It is also possible to synthesize backbone polymers which contain both hydrophilic and hydrophobic monomers.

Polymeric backbones of polymerizable macromers can optionally provide a number of desirable functions or attributes, e.g., as described in the above-captioned Hubbell patents, the disclosures of which are incorporated herein by reference. Backbones can be provided with water soluble regions, biodegradable regions, hydrophobic regions, as well as polymerizable regions.

As used herein, the term "polymerizable group" will generally refer to a group that is polymerizable by initiation by free radical generation, most preferably by photoinitiators activated by visible or long wavelength ultraviolet radiation. Preferred polymerizable groups include acrylates, methacrylates, ethacrylates, itaconates, acrylamides, methacrylamide, and styrene.

Typically, polymerizable groups are incorporated into a macromer subsequent to the initial macromer formation using standard thermochemical reactions. Thus, for example, polymerizable groups can be added to collagen via reaction of amine containing lysine residues with acryloyl chloride or glycidyl acrylate. These reactions result in collagen containing pendent polymerizable moieties. Similarly, when synthesizing a macromer for use as described in the present invention, monomers containing reactive groups can be incorporated into the synthetic scheme. For example, hydroxyethylmethacrylate (HEMA) or aminopropyl-methacrylamide (APMA) can be copolymerized with N-vinylpyrrolidone or acrylamide yielding a water-soluble polymer with pendent hydroxyl or amine groups. These pendent groups can subsequently be reacted with acryloyl chloride or glycidyl acrylate to form water-soluble polymers with pendent polymerizable groups.

Initiator groups useful in the system of the present invention include those that can be used to initiate, by free radical generation, polymerization of the macromers to a desired extent and within a desired time frame. Crosslinking and polymerization are generally initiated among macromers by a light-activated free-radical polymerization initiator. Preferred initiators for long wave UV and visible light initiation include ethyl eosin, 2,2-dimethoxy-2-phenyl acetophenone, other acetophenone derivatives, thioxanthone, benzophenone, and camphorquinone.

Preferred polymeric initiators are photosensitive molecules which capture light energy and initiate polymerization of the macromers. Other preferred polymeric initiators are thermosensitive molecules which capture thermal energy and initiate polymerization of the macromers.

Photoinitiation of the free radical polymerization of macromers of the present invention will generally occur by one of three mechanisms. The first mechanism involves a homolytic alpha cleavage reaction between a carbonyl group and an adjacent carbon atom. This type of reaction is generally referred to as a Norrish type I reaction. Examples of molecules exhibiting Norrish type I reactivity and useful in a polymeric initiating system include derivatives of benzoin ether and acetophenone.

The second mechanism involves a hydrogen abstraction reaction, either intra- or intermolecular. This initiation system can be used without additional energy transfer acceptor molecules and utilizing nonspecific hydrogen abstraction, but is more commonly used with an energy transfer acceptor, typically a tertiary amine, which results in the formation of both aminoalkyl radicals and ketyl radicals. Examples of molecules exhibiting hydrogen abstraction reactivity and useful in a polymeric initiating system, include analogs of benzophenone, thioxanthone, and camphorquinone.

When using a polymeric initiator of the hydrogen abstraction variety, pendent tertiary amine groups can be incorporated into the polymeric backbone of the macromer. This will insure that all free radicals formed are polymer-bound.

The third mechanism involves photosensitization reactions utilizing photoreducible or photo-oxidizable dyes. In most instances, photoreducible dyes are used in conjunction with a reductant, typically, a tertiary amine. The reductant intercepts the induced triplet producing the radical anion of the dye and the radical cation of the reductant. Examples of molecules exhibiting photosensitization reactivity and useful in a polymeric initiating system include eosin Y, rose bengal, and erythrosin. Reductants can be incorporated into the polymer backbone, thereby assuring that all free radicals will be polymer-bound.

Thermally reactive polymeric initiators are also useful for the polymerization of macromers. Examples of thermally reactive initiators usable in a polymeric initiating system include 4,4' azobis(4-cyanopentanoic acid) and analogs of benzoyl peroxide.

A surprisingly beneficial effect of the use of polymeric initiators to polymerize macromers is the increased efficiency of polymerization exhibited by these polymeric initiators as compared to their low molecular weight counterparts. This increased efficiency is seen in all three photoinitiation mechanisms useful for the polymerization of macromers.

Polymeric initiation of monomer solutions has been investigated for its application in the field of UV-curable coatings for industrial uses, c.f. U.S. Pat. No. 4,315,998 (Neckers) and PCT Application, International Publication No. WO 97/24376 (Kuester, et.al.) but there have been no reports of the adaptation of the use of polymeric initiators for the polymerization of macromers in the presence of biologic material or for the creation of drug-releasing matrices.

High efficiency of initiation is particularly important in systems such as these. It is generally desirable, when forming polymeric matrices in the presence of biologic or bioactive materials, to minimize the exposure time of the material to the energy source used to initiate polymerization. It is therefore imperative that the initiation system utilized possess optimum initiation efficiency.

When matrix strength or durability are required for a particular application, high efficiency is again a necessary characteristic of an initiation system. When a matrix-forming system is initiated, the free radical polymerization of the system is propagated until gelation and vitrification of the polymerizing system render the diffusion of the elements of the matrix-forming system too difficult. Therefore, the higher the efficiency of the initiation system, the more complete the polymerization resulting in the formation of stronger, more durable matrices. The polymeric initiation systems described in this invention provide a higher degree of efficiency, with or without the use of accelerants, than is attainable using nonpolymer-bound, low molecular weight initiators.

Another beneficial effect is realized when the initiating groups on the polymeric initiators consist of groups exhibiting hydrogen abstraction reactivity, i.e., the ability to abstract hydrogens intermolecularly. The beneficial effect is important when macromer systems containing these initiators are used as tissue adhesives, endovascular paving, formation of barriers to prevent post-surgical adhesions, or any application involving the "adhesion" of the matrix to one or more surfaces. Since initiators exhibiting this type of reactivity can abstract hydrogens from adjacent molecules, when a macromer system containing polymeric initiators of this type is applied to a substrate, photoactivation of the system causes the abstraction of hydrogens from the substrate by the initiators, thus forming a free radical on the substrate and a free radical on the initiator. This diradical can subsequently collapse forming a covalent bond between the macromer system and the substrate.

Other initiator groups on the same macromer initiate free radical reactions with other macromers resulting in the formation of a crosslinked matrix covalently bound to the surface. Initiator groups exhibiting this type of reactivity include analogs of benzophenone and thioxanthone. As can be readily understood, only polymeric initiators are capable of accomplishing this adhesion of the matrix to a surface, low molecular weight analogs of these initiators cannot produce this phenomenon.

Optionally, the use of initiators for initiating the necessary radical chain polymerization, can include the addition of one or more monomeric polymerization accelerants to the polymerization mixture, the accelerants serving to enhance the efficiency of polymerization. Polymerization accelerants useful in the present invention are typically monomers, which improve the reactivity of the macromer systems. Polymerization accelerants that have found particular utility for this application are N-vinyl compounds, particularly N-vinyl pyrrolidone and N-vinyl caprolactam. Such accelerants can be used, for instance, at a concentration of between about 0.01% and about 5%, and preferably between about 0.05% and about 0.5%, by weight, based on the volume of the macromer system.

In another embodiment, the polymeric initiator comprises a polymeric backbone with pendent initiator groups and pendent reactive or affinity groups. These reactive or affinity groups enable the polymeric initiator to bind to target groups on surfaces of interest. This allows the polymeric initiator to bind to the surface of interest. In this manner, interfacial polymerization of macromers can be accomplished. A solution of polymeric initiator-containing pendent reactive or affinity groups is applied to a surface with target sites. The reactive or affinity groups on the polymeric initiator react with the sites on the surface causing the polymeric initiator to bind to the surface. Excess polymeric initiator can then be washed away. A solution of a polymerizable macromer is then applied to the surface. When light energy in applied to the system, a free radical polymerization reaction is initiated only at the surface of interest. By varying the concentration of the polymerizable macromer and the illumination time, the thickness and crosslink density of the resulting matrix on the surface can be manipulated.

Generally, there are two methods by which an initiator group can be incorporated into a polymeric backbone. The first method involves the formation of a monomer which includes the initiator. This can be accomplished readily using standard chemical reactions. For example, the acid chloride analog of an initiator can be reacted with an amine-containing monomer, to form a monomer which contains the initiator.

The second method of incorporating initiator groups into a polymeric backbone involves coupling a reactive analog of the initiator with a preformed polymer. For example, an acid chloride analog of an initiator can be reacted with a polymer containing pendent amine groups forming a polymer bearing pendent initiator groups.

Macromer systems can be applied to a tissue site and/or implant article in any suitable manner, including by spraying, dipping, injecting or brushing the macromer system. Polymeric matrices prepared from macromer systems can be used in a variety of applications, including:

Cellular Encapsulation. The use of hydrogels to form micro- or macrocapsules containing cells and other tissue, is well documented in the literature. Applications include the treatment of diabetes, Parkinson's disease, Alzheimer's disease, ALS, chronic pain, and others. Descriptions of cellular encapsulation methods can be found throughout the patent and scientific literature. The use of the instant invention provides methods of encapsulating cells in two basic ways.

1) Bulk Polymerization

In this embodiment, cellular material is mixed in a solution of the macromer system and energy subsequently added to activate initiation of free radical polymerization. Prior to initiation, the solution containing the macromer system with suspended cellular material, can be placed in molds, shaped in particular geometric shapes, or placed inside a preformed membrane system, such as a hollow fiber. Upon illumination or other energy addition, the initiation of free radical polymerization causes the macromer system to gel, forming a cell-containing matrix in the desired shape. When formed into free-standing geometric shapes, the formulation of the macromer system can be designed to provide the desired degrees of durability and permselectivity to the subsequently formed matrix. When formed inside membrane structures, such as hollow fibers designed to provide the desired permselectivity, the macromer system can be formulated to provide the desired characteristics of the cell-suspending matrix, such as biocompatibility, etc.

2) Interfacial Polymerization

In this embodiment, a membrane is formed directly on the surface of the cellular material. A solution of polymerizable or non-polymerizable polymeric initiator-containing pendent affinity groups (e.g., positively charged groups) is mixed with the cellular material. The affinity groups bind to the sites on the surface of the cellular material. The excess polymeric initiator is subsequently washed away and the cellular material suspended in a solution of polymerizable macromer. Since initiator groups are present only at the surface of the cellular material, when light energy is applied, polymerization is initiated only at the surface:macromer interface. By manipulating the duration of illumination and macromer formulation, a polymeric matrix exhibiting the desired characteristics of thickness, durability, permselectivity, etc. is formed directly on the surface of the cellular material.

Adhesives and sealants. Polymeric matrix systems have also found extensive use as adhesives for tissue and other surfaces. For this application, a solution of a macromer system is applied to a surface to which adhesion is desired, another surface is contacted with this surface, and illumination is applied forming a surface-to-surface junction. If a temporary adhesive is desired, the macromer system can be composed of degradable macromers.

Barriers. Polymeric matrices can be used for the formation of barriers on surfaces for various applications. One such application is a barrier for the prevention of tissue adhesions following surgery. For this application, a macromer system in liquid form is applied to the surface of damaged tissue. The liquid is illuminated to polymerize the macromers. The polymeric matrix prevents other tissue from adhering to the damaged tissue. Both degradable and non-degradable macromer systems can be used for this purpose. As described above, both bulk polymerization and interfacial polymerization methods can be used to prepare surface coatings of this type.

Controlled Release Carriers. Polymeric matrices find wide application as controlled release vehicles. For this application, a solution of a macromer system and drug, protein, or other active substance is applied to a surface. The solution is illuminated to polymerize the macromers. The polymeric matrix contains the drug, when exposed to a physiological or other liquid-containing environment, the drug is slowly released into the environment. The release profile of the entrained drug can be manipulated by varying the formulation of the macromer system. Both degradable and non-degradable macromer systems can be utilized for this purpose. Likewise, both bulk and interfacial polymerization techniques can be used to prepare controlled drug-releasing surfaces. In an alternative embodiment, a drug or other active substance can be imbibed by a preformed matrix on a surface. The absorption and release characteristics of the matrix can be manipulated by varying the crosslink density, the hydrophobicity of the matrix, and the solvent used for imbibition.

Alternatively, drug-containing polymeric microspheres can be prepared using standard techniques. A wide range of drugs and bioactive materials can be delivered using the invention which include but are not limited to, antithrombogenic, anti-inflammatory, antimicrobial, antiproliferative, and anticancer agents, as well as growth factors, morphogenic proteins, and the like.

Tissue Replacement/Scaffolding. Polymeric matrices have found utility as three-dimensional scaffolding for hybrid tissues and organs. For this application, a macromer system in liquid form is applied to a tissue defect and subsequently illuminated to polymerize the macromers forming a matrix upon which ingrowing cells can migrate and organize into a functional tissue. In one embodiment, the macromer system additionally includes a growth factor which is slowly released and stimulates the ingrowth of desired cell types. In another embodiment, the macromers include pendent extracellular matrix peptides which can stimulate the ingrowth of desired cell types. A third embodiment would include both of the above features. An alternative embodiment includes cells included in the matrix with or without additional growth factor. The scaffolding can be generated in vitro by placing the liquid macromer system in a mold or cavities in a device, or can be generated in vivo by applying the liquid macromer system to a tissue defect. Both degradable and non-degradable macromer systems could be used for this application, but degradable matrices are preferred.

Wound Dressing. Polymeric matrices have been used extensively as superior wound dressing preparations. Currently, hydrogel and hydrocolloid wound dressing materials are being increasingly used due to their superior wound healing properties. For this application, a macromer system in liquid form is applied to the wound site and subsequently formed into a flexible polymeric matrix upon exposure to light. When applied as a liquid, the macromer preparation conforms to the irregular surface of the wound. Upon illumination, a flexible matrix is formed which is completely conformal to the surface of the wound; no fluid-filled pockets which can act as sites of bacterial infiltration can exist. In one embodiment, the macromer system additionally includes one or more therapeutic agents, such as growth factors or antimicrobial agents which are slowly released into the wound. Both degradable and non-degradable macromer systems can be used for this application.

In Situ Device Formation. Polymeric materials can be implanted into the body to replace or support the function of diseased or damaged tissues. One example of this is the use of hollow cylindrical polymeric devices to support the structure of a coronary artery following percutaneous transluminal coronary angioplasty (PTCA). Currently, preformed cylindrical devices are implanted via catheter insertion followed by balloon expansion to secure the device. The expanded device supports the structure of the artery and prevents the reversion of the artery to the closed position (restenosis).

For this application, a liquid macromer preparation could be applied to an injured artery via a multi-lumen catheter containing an illumination element. After application of the liquid macromer system to the injured tissue, a semi-rigid polymeric matrix can be formed by a brief illumination. Upon removal of the catheter, a hollow, cylindrical, conformal polymeric device remains to support the artery and prevent restenosis. In one embodiment, the macromer system additionally includes a releasable therapeutic agent or agents, such as antiproliferative and/or antithrombotic drugs. These agents are slowly released from the formed matrix, to provide additional therapeutic benefit to the injured tissues. Both degradable and non-degradable macromer systems can be used for this application.

The invention will be further described with reference to the following non-limiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight

EXAMPLES

Example 1

Synthesis of 7-Methyl-9-oxothioxanthene-3-carboxylic Acid Chloride (MTA-Cl)

The 7-methyl-9-oxothioxanthene-3-carboxylic acid (MTA), 50.0 g (0.185 mol), was dissolved in 350 ml of toluene and 415 ml (5.69 mol) of thionyl chloride using an overhead stirrer in a 2 liter 3-neck round bottom flask. N,N-Dimethylformamide (DMF), 2 ml, was added and the reaction was brought to reflux for 2 hours. After this time, the mixture was stirred at room temperature for 16 hours. The solvent was removed under vacuum and the product was azeotroped with 3×350 ml of toluene to remove the excess thionyl chloride. The product was recrystallized from 800 ml of chloroform and the resulting solid was placed in a vacuum oven for 16 hours at 45° C. to complete removal of solvent. The isolated product weighed 45.31 g (85% yield) and nuclear magnetic resonance spectroscopy (NMR) confirmed the desired structure. This product was used for the preparation of a photoreactive monomer as described in Example 2.

Example 2

Synthesis of N-[3-(7-Methyl-9-oxothioxanthene-3-carboxamido)propyl]methacrylamide (MTA-APMA)

The N-(3-aminopropyl)methacrylamide hydrochloride (APMA), 4.53 g (25.4 mmol), was suspended in 100 ml of anhydrous chloroform in a 250 ml round bottom flask equipped with a drying tube. After cooling the slurry in an ice bath, the MTA-Cl, 7.69 g (26.6 mmol), was added as a solid with stirring. A solution of 7.42 ml (53.2 mmol) of triethylamine (TEA) in 20 ml of chloroform was then added over a 1.5 hour time period, followed by a slow warming to room temperature. The mixture was allowed to stir 16 hours at room temperature under a drying tube. After this time, the reaction was washed with 0.1 N HCl and the solvent was removed under vacuum after adding a small amount of phenothiazine as an inhibitor. The resulting product was recrystallized from tetrahydrofuran (THF)/toluene (3/1) and gave 8.87 g (88.7% yield) of product after air drying. The structure of the compound was confirmed by NMR analysis.

Example 3

Preparation of N-Succinimidyl 6-Maleimidohexanoate (MAL-EAC-NOS)

6-Aminohexanoic acid, 100.0 g (0.762 moles), was dissolved in 300 ml of acetic acid in a three-neck, 3 liter flask equipped with an overhead stirrer and drying tube. Maleic anhydride, 78.5 g (0.801 moles), was dissolved in 200 ml of acetic acid and added to the 6-aminohexanoic acid solution. The mixture was stirred one hour while heating on a boiling water bath, resulting in the formation of a white solid. After cooling overnight at room temperature, the solid was collected by filtration and rinsed with 2×50 ml of hexane. After drying, the typical yield of the (Z)-4-oxo-5-aza-2-undecendioic acid was 158–165 g (90–95%) with a melting point of 160–1165° C. Analysis on an NMR spectrometer was consistent with the desired product.

(Z)-4-Oxo-5-aza-2-undecendioic acid, 150.0 g (0.654 moles), acetic anhydride, 68 ml (73.5 g, 0.721 moles), and phenothiazine, 500 mg, were added to a 2 liter three-neck round bottom flask equipped with an overhead stirrer. Triethylamine, 91 ml (0.653 moles), and 600 ml of THF were added and the mixture was heated to reflux while stirring. After a total of 4 hours of reflux, the dark mixture was cooled to <60° C. and poured into a solution of 250 ml of 12 N HCl in 3 liters of water. The mixture was stirred 3 hours at room temperature and then was filtered through a Celite 545 pad to remove solids. The filtrate was extracted with 4×500 ml of chloroform and the combined extracts were dried over sodium sulfate. After adding 15 mg of phenothiazine to prevent polymerization, the solvent was removed under reduced pressure. The 6-maleimidohexanoic acid was recrystallized from hexane/chloroform (2/1) to give typical yields of 76–83 g (55–60%) with a melting point of 81–85° C. Analysis on a NMR spectrometer was consistent with the desired product.

The 6-maleimidohexanoic acid, 20.0 g (94.7 mmol), was dissolved in 100 ml of chloroform under an argon atmosphere, followed by the addition of 41 ml (0.47 mol) of oxalyl chloride. After stirring for 2 hours at room temperature, the solvent was removed under reduced pressure with 4×25 ml of additional chloroform used to remove the last of the excess oxalyl chloride. The acid chloride was dissolved in 100 ml of chloroform, followed by the addition of 12.0 g (0.104 mol) of N-hydroxysuccinimide and 16.0 ml (0.114 mol) of triethylamine. After stirring overnight at room temperature, the product was washed with 4×100 ml of water and dried over sodium sulfate. Removal of solvent gave 24.0 g (82%) of MAL-EAC-NOS which was used without further purification. Analysis on an NMR spectrometer was consistent with the desired product.

Example 4

Preparation of a Copolymer of MTA-APMA, MAL-EAC-NOS, and N-Vinylpyrrolidone

A polymeric initiator is prepared by copolymerization of a monomer charge consisting of 5 mole % MTA-APMA, 10 mole % MAL-EAC-NOS, and 85 mole % N-vinylpyrrolidone (VP). The polymerization is run in formamide or other suitable solvent using 2,2'-azobisisobutyronitrile (AIBN) as an initiator and N,N,N',N'-tetramethylethylenediamine (TEMED) as an oxygen scavenger. Mercaptoethanol is added as a chain transfer reagent at a concentration designed to give a molecular weight between 2,000 and 20,000 daltons. Upon completion of the polymerization, the copolymer is precipitated by addition of ether or other non-solvent for the polymer. After isolation by filtration, the product is washed extensively with the precipitating solvent to remove residual monomers and low molecular weight oligomers. The copolymer is dried under vacuum and is stored desiccated to protect the hydrolyzable N-oxysuccinimide (NOS) esters.

Example 5

Synthesis of a Photoreactive Macromer Derived from a Poly(caprolactone-co-lactide) Derivative of Pentaerythritol Ethoxylate A 15 gram scale reaction was performed by charging a thick-walled tube with 8.147 g (56.5 mmol) of l-lactide (3,6-dimethyl-1,4-dioxane-2,5-dione) and 6.450 g (56.5 mmol) of ε-caprolactone. To this mixture was added 0.402 g (1.49 mmol) of pentaerythritol ethoxylate (ave. MW appprox. 270) to provide polymerization sites and control molecular weight. This mixture was warmed gently until dissolution of all reagents was complete. The catalyst, stannous 2-ethylhexanoate (0.015 ml) was added and the reaction vessel sealed. The reaction mixture was warmed to 150° C. and stirred for 20 hours. The resulting polymer was dissolved in chloroform and dialyzed against methanol using 1000 MWCO dialysis tubing. After dialysis, the solvent was removed in vacuo. The purified polymer was dissolved in chloroform and treated with 2.41 g (23.8 mmol) of TEA. To this reaction mixture was added 292 mg (1.19 mmol) of 4-benzoylbenzoyl chloride (BBA-Cl) and the resulting mixture was stirred for 16 hours. To this reaction mixture was added 0.734 g (8.11 mmol) of acryloyl chloride and the reaction was stirred an additional 8 hours. The modified polymer was purified by dialysis against methanol using 1000 MWCO dialysis tubing. After dialysis, the solvent was removed in vacuo and the polymer (15.36 grams) stored desiccated at room temperature.

Example 6

Synthesis of Water Soluble Siloxane Macromer with Pendent Initiator Groups

Fifty grams of a water-soluble siloxane macromer with pendent initiator groups were synthesized by first dissolving 50 grams of commercially available poly[dimethylsiloxane-co-methyl(3-hydroxypropyl)siloxane]-graft-poly(ethylene glycol) 3-aminopropyl ether (Aldrich Chemical) in 50 ml of methylene chloride. To this solution was added 5.0 g (49 mmol) of TEA. The reaction solution was cooled to −50° C., then transferred to a stir plate at room temperature. MTA-Cl, 1.0 g (3.5 mmol), prepared according to the general method in Example 1, and 5.0 g (55 mmol) of acryloyl chloride were added and the solution was stirred for 6 hours at room 1%) temperature. The solution was dialyzed against deionized water using 3500 MWCO dialysis tubing and the water was subsequently removed in vacuo. The product (48.4 grams) was stored desiccated at room temperature.

Example 7

Synthesis of a Polymerizable Hyaluronic Acid

Two grams of hyaluronic acid (Lifecore Biomedical, Chaska, Minn.) were dissolved in 100 ml of dry formamide. To this solution were added 1.0 g (9.9 mmol) of TEA and 4.0 g (31 mmol) of glycidyl acrylate. The reaction mixture was stirred at 37° C. for 72 hours. After exhaustive dialysis against deionized water using 12–14k MWCO dialysis tubing, the product (2.89 grams) was isolated by lyophilization.

Example 8

Preparation of a Photoderivatized Polyacrylamide (Photo-PAA)

Acrylamide, 10.24 g (0.144 mol), was dissolved in 200 ml of deionized water. To the solution was added 0.279 g (1.56 mmol) of APMA, 0.33 g (1.45 mmol) of ammonium persulfate and 0.155 g (1.33 mmol) of TEMED. The solution was evacuated in a filter flask with a water aspirator for 10 minutes. The tubing was clamped and the solution left under vacuum for one hour. The resulting polymer solution was dialyzed against deionized water using 12–14k MWCO dialysis tubing. To 150 ml of polymer solution in a PTFE bottle containing 3.0 grams of polymer was added 0.504 ml (3.62 mmol) of TEA. To this solution was added 30 ml of 28.4 mg/ml (3.48 mmol) 4-benzoylbenzoyl chloride in CHCl$_3$. The bottle was capped tightly and shaken for one hour. The bottle was then centrifuged for 10 minutes to separate the phases after which the aqueous layer was removed, dialyzed against deinoized water using 12–14k MWCO dialysis tubing, and lyophilized. The product (3.21 grams) was stored, dessicated at room temperature.

Example 9

Synthesis of the N-Hydroxysuccinimide Ester of Eosin Y

Eosin Y, 1.00 g (1.54 mmol), was dissolved in 10 ml dry dioxane with stirring, gentle warming and some sonication. After the solution was complete, the orange solution was cooled to room temperature under argon. N-Hydroxysuccinimide, 0.195 g (1.69 mmol), and 1,3-dicyclohexylcarbodiimide, 0.635 g (3.08 mmol), were added as solids. The resulting red mixture was stirred at room temperature for 48 hours under an inert atmosphere. After this time the solid was removed by filtration and washed with dioxane. The filtrate was concentrated in vacuo to give 1.08 g (94% yield) of a glassy red solid.

Example 10

Synthesis of a Copolymer of APMA, Methyl Methacrylate, and N-Vinylpyrrolidone Followed by Addition of Acryloyl Groups The following ingredients for the copolymer were placed in a glass vessel and dissolved in 20 ml DMSO: APMA (2.68 g, 15.0 mmol), VP (6.74 ml, 63.1 mmol), methyl methacrylate (mMA) (0.334 ml, 3.12 mmol), mercaptoethanol (0.053 ml, 0.76 mmol), AIBN (0.041 g, 0.25 mmol), and TEMED (0.057 ml, 0.38 mmol). After solution was complete, the monomer solution was degassed, blanketed with argon and placed in an agitating incubator at 55° C. The copolymer was dialyzed against deionized water in 6–8,000 MWCO dialysis tubing. The dialyzed solution (~400 ml) was loaded with acrylate groups. TEA, 5.0 ml (35.9 mmol), was added with stirring. The solution was placed in a freezer for 5–10 minutes to cool. After this time, 5.0 ml (61.5 mmol) of acryloyl chloride in 5 ml of chloroform were added with stirring. The reaction mixture was stirred at room temperature for 16 hrs. After this time the acrylated polymer was dialyzed against deionized water using 6–8,000 MWCO tubing. The product was lyophilized and 7.10 g were obtained.

Example 11

Synthesis of a Copolymer of MTA-APMA, APMA, Methyl Methacrylate, and N-Vinylpyrrolidone Followed by Addition of Acryloyl Groups The following ingredients for the copolymer were placed in a glass vessel and dissolved in 20 ml DMSO: MTA-APMA (0.613 g, 1.55 mmol), APMA (2.578 g, 14.4 mmol), VP (6.27 ml, 58.7 mmol), mMA (0.319 ml, 2.98 mmol), mercaptoethanol (0.054 ml, 0.77 mmol), AIBN (0.039 g, 0.24 mmol), and TEMED (0.053 ml, 0.35 mmol). After solution was complete, the monomer solution was degassed, blanketed with argon and placed in an agitating incubator at 55° C. The copolymer was dialyzed against deionized water in 6–8,000 MWCO dialysis tubing. The dialyzed solution was protected from light and loaded with acrylate groups. TEA, 5.0 ml (35.9 mmol), was added with stirring. The solution was placed in a freezer for 5–10 minutes to cool. After this time, 5.0 ml (61.5 mmol) of acryloyl chloride in 5 ml of chloroform were added with stirring. The reaction mixture was stirred at room temperature for 9 hrs. After this time the acrylated polymer was dialyzed against deionized water using 6–8,000 MWCO tubing and protected from light. The product (8.88 grams) was isolated by lyophilization.

Example 12

Evaluation of Matrix Formation

A 15% solution of the co-polymer from Example 11 was prepared in 10% DMSO/ water. The MTA content of the solution was estimated by measuring the absorbance of the solution at 395 nm (A@395 nm=42.6). A 15% solution of the co-polymer from Example10(same co-polymer as that described in Example 11 but with no MTA-APMA) was prepared in 10% DMSO/water. MTA was added to this solution until its absorbance at 395 nm matched that of the solution described above. The two solutions were identical in concentration of co-polymer and photoinitiator, the only difference between them being that in one solution the photoinitiator was present in polymeric form(POLY) and in the other the photoinitiator was present in non-polymeric form(NON).

In order to compare the matrix forming ability of the two solutions the following evaluation was undertaken: the indentations in the lid of a 96 well microtiter plate were used as miniature molds to evaluate the ability of the photoreactive polymer solutions to form solid hydrogel discs upon illumination. The indentations are eight millimeters in diameter and approximately 0.6 millimeters deep. 30 microliters of polymer solution will just fill the indentatation. Thirty microliters of both the (POLY) and (NON) solutions were added to wells. After addition of the polymer solutions, the lids were illuminated using an EFOS Ultracure 100 illumination system equipped with a 400–500 nm filter, for varying lengths of time. After illumination the lid was flooded with water and each polymer formulation rated for its ability to form solid discs using the following arbitrary scale:

0=liquid, no gelation
1=soft gel, unable to remove from mold
2=firm gel, removable from mold with slight difficulty
3=very firm gel, easily removed from mold
4=very firm gel, elastomeric properties evident Results:

| Polymer | Time(sec) | | | | | |
|---|---|---|---|---|---|---|
| | 2 | 5 | 10 | 30 | 60 | 120 |
| (POLY) | 1 | 2 | 3 | 4 | 4 | 4 |
| (NON) | 0 | 0 | 1 | 2 | 3 | 3 |

Matrix formation

The polymer solution containing the polymer-bound initiator(POLY) formed matrices more rapidly and more completely than the polymer solution containing non-polymer-bound initiator(NON) when exposed to light energy.

Example 13

Synthesis of an Eosin Substituted Polymer

N-Vinylpyrrolidone, 10.0 g (90.0 mmol), was dissolved in 50 ml DMSO. To the solution was added 0.30 g (1.68 mmol) of APMA, 0.15 g (0.91 mmol) of AIBN, and 0.10 g (0.86 mmol) of TEMED. The solution was sparged with nitrogen for 20 minutes and incubated at 55° C. for 20 hours. The resulting polymer was purified by dialysis against water and isolated by lyophiliaztion.

Three grams of the polymer were dissolved in 150 mls dry dioxane. To this solution was added 0.504 ml (3.62 mmoles) of TEA. Subsequently, 2.74 grams (3.5 mmoles) of the N-hydroxysuccinimide ester of Eosin Y was added and the reaction mixture stirred for two hours at room temperature. The solution was dialyzed against $dH_2O$ using 12–14 kda cut-off dialysis tubing and lyophilized to isolate the product. The reaction yielded 3.96 grams of red polymer.

Example 14

A Biodegradable Tissue Adhesive

A solution was prepared consisting of 5% polymerizable hyaluronic acid (Example 7) and 2% photoderivatized polyacrylamide (Example 8) in water. This reagent was evaluated for use as a tissue adhesive using cellulose dialysis tubing as a tissue model.

Shear strength testing was performed on dialysis tubing. The tubing was slit and cut into 2 cm×4 cm pieces. The pieces were soaked in water briefly, removed, and tested while still damp. One piece was laid flat on a surface and 10 µl of adhesive applied to one end of the strip. Another piece was laid over this piece with a 1 cm overlap between pieces. When evaluating the photoactivatable adhesive (2/5 HA), the overlap area was illuminated for 10 seconds. When evaluating a control adhesive, the adhesive was allowed to set for five minutes. The bonded samples were mounted in a tensiometer lengthwise by the ends such that the plane of the area of adhesive was parallel to the axis of the tensiometer. The samples were extended at the rate of 1 cm/minute until adhesive or substrate failure, and the force at failure recorded. Substrate-only, and, for photoactivatable adhesive, non-illuminated samples, were included as controls in the evaluations.

| Adhesive | Maximum Force Generated Kg | Adhesive Failed Before Substrate | Substrate Failed Before Adhesive |
|---|---|---|---|
| 2/5 HA | 0.53 | 0/4 | 4/4 |
| 2/5 HA (no illumination) | 0.081 | 4/4 | 0/4 |
| Fibrin glue | 0.045 | 4/4 | 0/4 |
| Cyanoacrylate | 0.49 | 0/4 | 4/4 |

Example 15

Formation of an in situ Hydrogel Wound Dressing

Photopolymerizable, matrix-forming reagents were evaluated for efficacy as in situ wound dressings.

Preparation of Reagents:

An experimental in situ forming wound dressing was prepared by:

1) Dissolving reactive macromer from Example 10 at 20% into a sterile 6% glycerin solution in water.

2) Preparing a sterile solution of polymeric eosin reagent from Example 12 at 4% in water and a sterile solution of 2M triethanolamine (TEA) in water.

3) Transporting the three sterile solutions to a surgical suite for application to wound sites created on porcine skin.

Four young female China White swine weighing between 15–20 kg were anesthetized and 12 wounds inflicted on one side of each pig. Wounds were 1"×2" and 0.015" deep and were inflicted by a calibrated electrodermatome (Padgett). The wounds were inflicted in two rows of six on the thoracic and paravertebral area of each pig, leaving approximately two inches between adjacent wounds. The wounds were randomized and received one of three treatments:

1) No treatment (control)

2) Application of OpSite®, a semi-occlusive wound dressing from Smith and Nephew, Inc.

3) Experimental photo-curable dressing

To apply the experimental dressing, 0.5 mls of the polymeric-eosin solution and 0.5 mls of the TEA solution were added to the macromer/glycerin solution yielding a photo-wound dressing solution. The solution was transferred to 16 three ml sterile syringes (2 ml/syringe) and one syringe was used to application to each wound site. The solutions were applied to each assigned wound site (approximately 1.5 mls solutions/site) and allowed to flow over the site. The solutions were fixed by illumination with a 150 W incandescent light bulb positioned four inches from the wound surface for 30 seconds. The dressing solution readily formed into a durable, rubbery hydrogel which adhered very well to the wound sites. Sterile 4×4 gauze pads were placed over the entire wounded area of each pig, and the pigs placed in sterile stockinettes. On selected days (3, 4, 5, and 7), one pig was euthanized and the effect of dressing on wound epithelialization and repair evaluated.

Evaluation of effect of dressing on wound epithelialization and repair:

Following euthanasia, skin wounds were removed from the underlying deep subcutaneous tissue and fixed in 10% neutral buffered formalin solution. After fixation, five biopsy sites from each wound were obtained with a 6 mm Keys skin biopsy punch. Each biopsy was packaged, labeled and submitted for histological sectioning. Histological sections were sectioned at 4 microns and stained with hematoxylin and eosin. Histological sections were examined with the microscope without knowing the type of covering placed over the wound site.

The Following Criteria were Evaluated and Scored in Microscopic Examination:

Degree of epithelialization of the wound

Magnitude of the inflammatory reaction

Degree of fibroplasia in the wound

Degree of damage to subcutaneous tissue:

Morphometric analysis of cell types in the histological sections were used to help differentiate the degree of inflammatory reaction present. The number of polymorphonuclear cells, lymphocytic cells, and fibroblasts was evaluated. Each histological biopsy was graded on a scale of 1–5.

Degree of Inflammatory Reaction:

1. No or borderline cellular inflammatory reaction

2. Minimal inflammation

3. Moderate density of inflammatory cells with some exudate

4. Severe, high density of inflammatory cells in or on the wound tissue with thicker layer of exudate 5. Excessive inflammation, with signs of dense foci of inflammatory cells infiltrating the wound tissue or on the wound and forming a thick layer of inflammatory exudate.

Degree of Wound Epithelialization:
1. Stratum corneum present at least 4 layers of cells and entire epidermal surface is present.
2. Stratum corneum is present at least 1 layer of cells and entire epidermal surface is present.
3. Stratum corneum is present at least 1 layer of cells and ½ of epidermal surface is covered.
4. No stratum corneum is present; minimal inflammation of the subepidermal tissue.
5. No stratum corneum is present; moderate inflammation in subepidermal tissue.

Degree of Fibroplasia in the Wound:
1. No fibroplasia in the wound
2. Mild fibroplasia in the wound involving ⅓ to ½ wound surface
3. Mild fibroplasia in the wound involving ⅔ or more of the wound
4. Moderate fibroplasia involving ⅓ to ½ of the wound
5. Severe fibroplasia involving ½ or more of the wound Degree of Damage to the Subcutaneous Tissue:
1. No damage to the subcutaneous tissue
2. Mild damage to the subcutaneous tissue with mild edema and few inflammatory cells.
3. Moderate damage to the subcutaneous tissue with moderate edema and moderate accumulation of inflammatory cells
4. Severe damage to the subcutaneous tissue with severe edema and large number of inflammatory cells
5. Excessive damage to the subcutaneous tissue with dense foci of inflammatory cells Results:

Each biopsy was graded blindly using the criteria listed above. When the histological examination was completed, the graded biopsies were correlated with the wound sites. A single average score for each dressing was calculated by adding all the scores for every site for each dressing and dividing by the number or scores.

The total scores for each type of wound dressing on days 3, 4, 5, and 7 were evaluated with an ANOVA SAS program for data intervals to statistically evaluate if there was any difference between the three types of wound treatments administered. Only two scores were found to be statistically significant:

1. On day 4 following wound creation the mean for the OpSite® dressing was 2.4 and was found to be statistically significant when compared to the control and experimental wound sites.
2. On day 7 following the creation of the wounds the mean for the experimental dressing, 1.8 was found to be statistically significant when compared to the control and the OpSite® wound dressings.

On day 7 post-wound creation, the wound sites treated with the experimental photocurable dressing showed significantly superior healing to those that were untreated or treated with OpSite® dressing, as judged by the criteria described.

Example 16

A Bioresorbable Drug Delivery Coating

A solution of 33% of the macromer from Example 5 was prepared in ethanol. Ten centimeter lengths of polyurethane rod (PU) were dipped into the macromer solutions and illuminated for six minutes to form a matrix. This procedure resulted in the formation of a very durable, tenacious, and flexible coating on the rod. One gram of chlorhexidine diacetate (an antimicrobial agent) was dissolved in 10 mls of the macromer solution and the coating process repeated on additional PU rods. This also resulted in a tenacious, durable, and flexible coating on the rods. The rods were cut into one centimeter pieces and evaluated in a zone of inhibition analysis.

Coated dye-containing pieces, coated no-drug controls, and uncoated pieces were placed in Mueller-Hinton agar plates which were swabbed with a $10^6$ suspension of Staphylococcus epidermidis (Christensen RP62A). These pieces functioned as unwashed controls and were transferred to freshly swabbed agar plates each day for 60 days.

Additional pieces, no-drug controls (both coated and uncoated) and drug-incorporated coated, wer placed in snap-cap vials and washed with 50% Normal Calf Serum in PBS. The tubes were placed on an orbital shaker and incubated at 37° C. and 200 rpm for 20 days. Each day the wash solution was removed and replaced with fresh solution. Periodically, pieces were removed from the serum/PBS and placed in agar as described above. Zones of inhibition resulting from these pieces were recorded and compared to the zones produced by unwashed pieces.

The no-drug coated control pieces, both coated and uncoated, produced no zones. On day 0, both washed and unwashed drug-incorporated pieces produced zone of 24.5 mm. On day 20, when the final washed pieces were evaluated, the unwashed pieces were producing zones of 17.5 mm, and the washed pieces were producing zones of 9.5 mm. On day 60, when the experiment was terminated, the unwashed pieces were still producing zones of 17 mm.

This experiment demonstrates the utility of this matrix-forming polymer at producing drug delivery coatings which provide a long-term delivery of a bioactive agent.

Example 17

A Biostable Drug Delivery Coating

A solution of 25% of the macromer from Example 6 was prepared in 50% IPA/H$_2$O. Ten centimeter lengths of polyurethane rod were dipped into the macromer solution and illuminated for six minutes to form matrix. This procedure resulted in the formation of a very durable, tenacious, and flexible coating on the rod. Five hundred milligrams of chlorhexidine diacetate was dissolved in 10 mls ethanol. Half of the coated rods were soaked in this solution for 60 minutes at room temperature, and half of the rods were soaked in neat ethanol under the same conditions. After soaking, the rods were removed from the ethanol and allowed to dry for 20 hours at room temperature. The rods were cut into one centimeter pieces and evaluated in a zone of inhibition analysis.

Uncoated control, coated control, and coated drug-incorporated pieces were placed in Mueller-Hinton agar plates which were swabbed with a $10^6$ suspension of Staphylococcus epidermidis (Christensen RP62A). These plates were incubated for 20 hours at 37° C. The zone where no bacterial growth was evident around each piece was measured and the piece transferred to a freshly swabbed agar plate each day for 14 days.

The uncoated control pieces and the coated control pieces produced no zones. On day 0, the drug-incorporated coated pieces produced average zones of 25 mm. These pieces continued to produce zones each day. On day 14, when the experiment was terminated, the pieces produced average zones of 6 mm.

Example 18

Formation of a Three-Dimensional Device

One end of a 3 mm diameter teflon-coated rod was dipped to a level of 1.5 cm in neat BBA-acryloylpolytetra (caprolactone-co-lactide)pentaerythritol ethoxylate (see Example 5) and immediately illuminated, with rotation, for 10 seconds suspended between opposed Dymax lamps. After illumination, a semi-rigid elastomeric coating had formed on the rod. The rod was cooled to facilitate removal of the polymeric coating. The closed end of the cylinder was removed with a razor blade, thus forming a hollow cylindrical device of 1.25 cm in length and 3.5 mm in diameter.

Example 19

Synthesis of a Polymerizable Collagen

One gram of soluble collagen (Semed-S, Kensey-Nash Corp.) (a mixture of Types I and III) was dissolved in 50 mls of 0.01 N HCl. When dissolved, 1.25 gms triethylamine (12.4 mmoles) was added to the reaction mixture. One gram of acryloyl chloride (11.0 mmoles) dissolved in one milliliter of methylene chloride was added to the reaction vessel and the mixture was stirred for 20 hours at room temperature.

The reaction mixture was dialyzed exhaustively against $dH_2O$, and the product isolated by lyophilization. A yield of 1.17 grams of polymerizable collagen was realized.

Example 20

A Collagen Scaffolding that Contains a Bone Morphogenic Protein

A. Preparation of the Solidified Scaffolding.

A solution of liquid macromer is prepared which consists of 5% (w/v) of polymerizable collagen (Example 19) plus 1% (w/v) of photoderivatized polyacrylamide (prepared as described in Example 8) in phosphate buffered saline, pH 7.4. To this is added 50 fig/ml (0.005% w/v) of bone morphogenic protein (BMP-7 from a private source). Aliquots of the above solution (150 µl) are then placed in molds (8 mm diameter and 3 mm high) and are illuminated for 10 seconds with a Dymax lamp (as described in Example 13) to solidify the collagen scaffolding. Control disks of solidified collagen scaffolding are prepared via the same protocol except that BMP-7 is not added.

B. Evaluation of the Solidified Scaffolding.

Disks of solidified collagen scaffolding with BMP-7 are evaluated for stimulation of bone growth in a rat cranial onlay implant model. In this model, the periosteal membrane is removed and the collagen disks are implanted on the cranium. After 30 days, the implants and adjacent cranial bone are removed, fixed in cold methanol, embedded in PMMA, sectioned, ground to 50–100 µm thickness, stained with Sandersons Rapid Bone Stain, and counterstained with Van Gieson's picro-fuchsin. This protocol evaluates nondecalcified bone, with mature bone staining red, immature bone staining pink, cartilage staining blue-gray, and undegraded collagen appearing acellular and pale yellow.

One control consists of disks of solidified collagen scaffolding lacking BMP-7. A second control consists of 150 µl of nonilluminated liquid macromer solution which contains BMP-7 (the same solution composition that was placed in molds and illuminated to produce the solidified collagen scaffolding containing BMP-7).

When evaluated histologically at 30 days as described above, the experimental disks (solidified collagen scaffolding containing BMP-7) show extensive bone formation in the space originally occupied by the collagen disk. In contrast, both controls (the solidified collagen scaffolding lacking BMP-7 and the nonilluminated liquid control solution containing BMP-7) show little or no bone formation. The amount of bone that forms with the controls is less than 25% of that observed with the experimental disks, therefore demonstrating that the solidified collagen scaffolding greatly enhances BMP-stimulated bone formation.

Example 21

Synthesis of a Polymerizable Collagen

Dissolved 0.5 gram collagen (insoluble bovine tendon collagen, Type I, ReGen Corp.) in 20 mls dry formamide by incubating for 20 hours on an orbital shaker at 37 degrees C. With stirring, added 1.0 gram (9.8mmol) TEA and equilibrated for 60 minutes in ice water bath. With stirring, added 1.0 gram (11 mmol) acryloyl chloride, in 0.25 gram aliquots (1 aliquot/min). After the final addition, stirred in ice water bath for 2 hours. Removed from ice water bath and continued to stir at room temperature for 18 hours. The product was purified by dialysis against deionized water using 6–8K MWCO dialysis tubing, and isolated by lyophilization.

What is claimed is:

1. A method of delivering an implant article to a tissue site, the method comprising
   a) providing an implant article selected from the group consisting of tissue implants and prosthetic devices providing a porous surface,
   b) providing a matrix-forming system comprising a polymerization initiator and a crosslinkable macromer comprising one or more polymers having pendent polymerizable groups,
   c) implanting the article within the tissue site with the matrix-forming system positioned between the article and the tissue site, and
   d) polymerizing the matrix-forming system to form a crosslinked matrix between the article and the tissue site suitable to permit continuous tissue growth through the matrix and between the implant article and the tissue site.

2. A method according to claim 1 wherein the matrix-forming system is positioned upon the article prior to implanting the article within the tissue site and is crosslinked before, during or after implanting the article within the tissue site.

3. A method according to claim 1 wherein the matrix-forming system is delivered to the tissue site and crosslinked before, during or after the implant article has been positioned within the tissue site.

4. A method according to claim 1 wherein a first amount of a matrix-forming system is positioned upon the article prior to implanting the article within the tissue site, and a second amount of either the same or a different matrix-forming system is delivered to the tissue site, either before or after positioning the implant article within the tissue site, and the first and second amounts are independently crosslinked before, during or after positioning the implant within the tissue site.

5. A method according to claim 1 wherein the matrix-forming system is applied to the tissue site and/or implant article by spraying, dipping, injecting or brushing the matrix-forming system.

6. A method according to claim 1 wherein the polymer having pendent polymerizable groups is prepared by a method that comprises the steps of
   a) providing a polymer selected from the group consisting of polysaccharides and polyamino acids, and
   b) incorporating polymerizable groups into the polymer by reaction of the polymer with a reactive moiety containing an ethylenically unsaturated group capable of undergoing free radical polymerization,
      wherein the reaction between the polymer and reactive moiety is carried out in a medium comprising a polar organic solvent.

7. A method according to claim 6 wherein the polysaccharides are selected from the group consisting of hyaluronic acid, starch, dextran, heparin, chondroitin sulfate, dermatan sulfate, heparan sulfate, keratan sulfate, dextran sulfate, pentosan polysulfate, and chitosan, and the polyamino acids are selected from the group consisting of gelatin, collagen, fibronectin, laminin, albumin, elastin, and active peptide domains thereof.

8. A method according to claim 7 wherein the solvent comprises formamide.

9. A method according to claim 8 wherein the reactive moiety is selected from the group consisting of glycidyl acrylate and acryloyl chloride.

10. A method according to claim 9 wherein the polymer comprises hyaluronic acid or collagen.

11. A method according to claim 1 wherein the initiators comprise polymer-pendent initiators.

12. A method according to claim 1 wherein the matrix-forming system further comprises a polymerization accelerator comprising a N-vinyl compound.

13. A method according to claim 1 wherein the article is selected from the group consisting of joint implants, dental implants, soft tissue cosmetic prostheses, wound dressings, vascular prostheses, and ophthalmic prostheses.

14. A method according to claim 13 wherein the article is a joint implant selected from the group consisting of hip and knee prosthetic devices having porous surfaces.

15. A method according to claim 14 wherein the prosthetic device is fabricated from synthetic materials and the porous surface provides a three-dimensional structure having interconnected passages, with pores having an average pore size of between about 5 microns and about 1 mm in diameter.

16. A method according to claim 15 wherein the average pore size is between about 20 microns and about 600 microns in diameter.

17. An implantable combination comprising
   a) an implant article selected from the group consisting of tissue implants and prosthetic devices providing a porous surface, and
   b) a matrix-forming system positioned upon the article and comprising a polymerization initiator and a crosslinkable macromer comprising one or more polymers having pendent polymerizable groups.

18. A combination according to n the matrix-forming system is crosslinked to form a matrix suitable to permit continuous tissue growth through the matrix and between the implant and a tissue site.

19. An implanted combination comprising
   a) an implant article selected from the group consisting of tissue implants and prosthetic devices providing a porous surface, and
   b) a crosslinked matrix positioned between the article and the tissue site, the matrix.

20. An implanted combination comprising
   a) an implant article selected from the group consisting of tissue implants and prosthetic devices providing a porous surface,
   b) a crosslinked matrix positioned between the article and the tissue site, the matrix prepared by crosslinking a matrix-forming system comprising a polymerization initiator and a crosslinkable macromer comprising one or more polymers having pendent polymerizable groups, wherein the combination is positioned within and/or in apposition to a tissue site, and wherein continuous tissue ingrowth is present through the matrix and between the tissue site and the implant article.

* * * * *

UNITED STATES PATENT AND TRADEMARK OFFICE
CERTIFICATE OF CORRECTION

PATENT NO. : 6,410,044 B1
APPLICATION NO. : 09/571525
DATED : June 25, 2002
INVENTOR(S) : Chudzik et al.

Page 1 of 1

It is certified that error appears in the above-identified patent and that said Letters Patent is hereby corrected as shown below:

a. Claim 18, line16 replace "n" with -- claim 17, wherein --.
b. Claim 19, line 26 please add the following after the word "matrix" -- prepared by crosslinking a matrix-forming system comprising a polymerization initiator and a crosslinkable macromer comprising one of more polymers having pendent poylmerizable groups, wherein the combination is positioned within and/or in apposition to a tissue site.--.

Signed and Sealed this

Second Day of January, 2007

JON W. DUDAS
*Director of the United States Patent and Trademark Office*